United States Patent
Miller et al.

(10) Patent No.: US 8,143,457 B2
(45) Date of Patent: Mar. 27, 2012

(54) PROCESS OF REFINING $C_6$-$C_{16}$ ALIPHATIC DIOLS

(75) Inventors: Glenn A. Miller, South Charleston, WV (US); Edward H. Yonemoto, Houston, TX (US); Rainer Potthast, Houston, TX (US)

(73) Assignee: Dow Global Technologies LLC

( * ) Notice: Subject to any disclaimer, the term of this patent is extended or adjusted under 35 U.S.C. 154(b) by 34 days.

(21) Appl. No.: 12/669,124

(22) PCT Filed: Jul. 7, 2008

(86) PCT No.: PCT/US2008/069308
§ 371 (c)(1),
(2), (4) Date: Jun. 9, 2010

(87) PCT Pub. No.: WO2009/017936
PCT Pub. Date: Feb. 5, 2009

(65) Prior Publication Data
US 2010/0267997 A1   Oct. 21, 2010

Related U.S. Application Data

(60) Provisional application No. 60/962,548, filed on Jul. 30, 2007.

(51) Int. Cl.
C07C 31/20 (2006.01)

(52) U.S. Cl. .................................................. 568/831
(58) Field of Classification Search ............... 568/831
See application file for complete search history.

(56) References Cited

U.S. PATENT DOCUMENTS

| | | | |
|---|---|---|---|
| 2,626,284 A | 1/1953 | Smith et al. |
| 2,753,297 A | 7/1956 | Mason |
| 2,889,375 A | 6/1959 | Gilbert et al. |
| 3,359,335 A | 12/1967 | Roming |
| 3,689,371 A | 9/1972 | Kerber et al. |
| 3,960,672 A | 6/1976 | Ester et al. |
| 6,117,277 A | 9/2000 | Zgorzelski et al. |
| 6,252,121 B1 | 6/2001 | Argyropoulos et al. |
| 6,632,331 B2 | 10/2003 | Yoshida et al. |

FOREIGN PATENT DOCUMENTS

DE    10258318    6/2004

*Primary Examiner* — Sikarl Witherspoon

(57) ABSTRACT

A process of refining a crude $C_6$-$C_{16}$ aliphatic diol, preferably, a $C_6$-$C_{16}$ monocyclic aliphatic diol, more preferably, an isomeric mixture of cis/trans-(1,3)(1,4)-cyclohexanedimethanol, containing in addition to the diol one or more impurities selected from phenols, and aliphatic mono-ols, esters, carboxylic acids, and hemiacetals, and mixtures thereof. The refining process involves distilling the crude C6-C16 aliphatic diol in the presence of an alkali or alkaline earth metal compound, preferably, an excess thereof relative to acid equivalents present in the diol.

19 Claims, No Drawings

PROCESS OF REFINING $C_6$-$C_{16}$ ALIPHATIC DIOLS

CROSS REFERENCE TO RELATED APPLICATIONS

This application is a 371 of PCT/US2008/069308 filed Jul. 7, 2008, which claims the benefit of U.S. Provisional Application Ser. No. 60/962,548, filed Jul. 30, 2007.

BACKGROUND OF THE INVENTION

The present invention relates to a process of refining a $C_6$-$C_{16}$ aliphatic diol. More particularly, the process pertains to separating a purified $C_6$-$C_{16}$ aliphatic diol from a crude mixture containing the $C_6$-$C_{16}$ diol and one or more impurities selected from phenols, and aliphatic mono-ols, esters, carboxylic acids, hemiacetals, and mixtures thereof.

The aliphatic diols refined by the process of this invention find utility in the manufacture of plasticizers and as chain-extenders in the manufacture of polyurethanes.

As synthesized, $C_6$-$C_{16}$ aliphatic diols, preferably, $C_6$-$C_{16}$ alicyclic diols, such as, cis/trans 1,3- and 1,4-cyclohexanedimethanol, typically contain one or more impurities selected from the following classes of aliphatic compounds: mono-ols, esters, carboxylic acids, and hemiacetals, as well as impurity aromatic phenols, and mixtures of the aforementioned compounds. These impurities may be present in the starting materials from which the diol is prepared; or the impurities may be generated as side products during the process of preparing the diol. Diols derived from the hydrogenation of aldehydes, which themselves are generated by hydroformylation of olefins, are particularly susceptible to containing such impurities.

In a commercial example of the above, a cis, trans mixture of 1,3 and 1,4-cyclohexanedimethanol isomers (hereinafter referred to as "cis/trans-(1,3)(1,4)-cyclohexanedimethanol") is typically prepared by first reacting 1,3-butadiene with acrolein in a Diels Alder reaction to form 3-cyclohexene-1-carboxaldehyde; and thereafter hydroformylating 3-cyclohexene-1-carboxaldehyde with a mixture of carbon monoxide and hydrogen (synthesis gas or syngas) to prepare cis/trans-(1,3)(1,4)-cyclohexane-dicarboxaldehyde, which is then hydrogenated in the presence of a hydrogenation catalyst to the crude aliphatic diol comprising cis/trans-(1,3)(1,4)-cyclohexanedimethanol and one or more of the aforementioned mono-ol, ester, carboxylic acid, hemiacetal, and/or phenol impurities. Preferably, the crude aliphatic diol is distilled to recover a purified cis/trans-(1,3)(1,4)-cyclohexanedimethanol product.

By analyzing various steps in the diol synthesis the skilled person may perceive the origins of the various impurities, although the invention described herein should not be bound to such theory. Hydroformylations are usually conducted in the presence of a rhodium-organophosphite ligand complex catalyst. As a side reaction, undesirable hydrolysis of the phosphite ligand may result in formation of impurity phenols. Impurity aliphatic mono-ols, such as cyclohexanemethanol and cyclohexenemethanol, may form as a side product of hydrogenation of the intermediate mono-aldehyde, for example, hydrogenation of cyclohexene-1-carboxaldehyde. Impurity carboxylic acids may be formed by oxidation of the aldehyde compositions or generated by hydrolysis of impurity esters. Impurity esters and hemiacetals may be derived from heavies that are present during distillation of crude aldehyde products.

Distillation of the crude $C_6$-$C_{16}$ aliphatic diol does not adequately remove the impurities, which may be sufficiently volatile to distill with the diol. Moreover, at a temperature sufficient for distillation, acidic impurities can catalyze formation of additional impurities through cracking of heavies, thereby increasing the overall quantity of impurities during the very distillation process that is intended to refine the diol. Acid impurities can also lead to corrosion of the distillation equipment. As a consequence, it would be desirable to discover a method of separating a purified $C_6$-$C_{16}$ aliphatic diol from a crude $C_6$-$C_{16}$ aliphatic diol contaminated with one or more impurities, particularly, those selected from aliphatic mono-ols, esters, carboxylic acids, and hemiacetals, as well as impurity aromatic phenols, and mixtures of the aforementioned compounds.

U.S. Pat. No. 6,632,331 discloses removal of aldehyde compounds contained as impurities in polycyclic diols by distilling the polycyclic diols in the presence of an alkali metal compound and/or an alkaline earth compound.

U.S. Pat. No. 6,117,277 discloses purification of $C_3$-$C_{10}$ straight-chain or branched mono-alcohols by distilling the alcohol at 150-200° C. in the presence of alkali metal hydroxide so as to remove impurity aldehydes.

U.S. Pat. No. 3,359,335 discloses purification of an alcohol product obtained by the catalytic carbonylation of an olefin with carbon monoxide and hydrogen to give a reaction mixture made up of carbonyl compounds, followed by catalytic hydrogenation to convert the carbonyl compounds to the alcohol product contaminated with high boiling esters, acetals, ethers, and decomposition products boiling within the boiling range of the alcohol. The purification involves scrubbing the crude alcohol product with an aqueous caustic solution, thereafter washing the scrubbed product to remove the caustic solution, and then distilling the washed product to recover a purified alcohol. Since polyols have appreciable solubility in water, significant product losses can result.

SUMMARY OF THE INVENTION

This invention provides for a process of refining a crude $C_6$-$C_{16}$ aliphatic diol. More specifically, the process comprises distilling one or more times a crude $C_6$-$C_{16}$ aliphatic diol comprising, in addition to the diol, one or more impurities selected from phenols and aliphatic mono-ols, esters, carboxylic acids, hemiacetals, and mixtures thereof, in the presence of an alkali metal compound and/or an alkaline earth metal compound under conditions sufficient to obtain a purified $C_6$-$C_{16}$ aliphatic diol.

According to the invention, there is provided herein a process of refining a crude $C_6$-$C_{16}$ aliphatic diol via distillation in the presence of an alkali metal compound and/or an alkaline earth metal compound to recover a purified $C_6$-$C_{16}$ aliphatic diol. Surprisingly, the presence of alkali metal compound and/or alkaline earth metal compound under distillation conditions does not increase side reactions or destruction of the diol, but rather facilitates efficient separation and recovery of desired diol product having significantly improved purity as compared with the crude diol. Moreover, the use of alkali metal compound and/or alkaline earth metal compound in the subject distillation described herein may reduce the total number of distillations needed to obtain a diol product of acceptable purity for commercial use. Commercial aliphatic diol beneficially contains a total acidity of less than about 500 parts per million (ppm), calculated as acetic acid and based on the weight of the aliphatic diol product. Moreover, commercial diol product should appear colorless or nearly colorless, as explained hereinafter, because color typically indicates the presence of unwanted impurities. As a further benefit, reduction of acid during distillation can correlate with reduced corrosion of the distillation equipment.

DETAILED DESCRIPTION OF THE INVENTION

References to the Periodic Table of the Elements herein shall refer to the Periodic Table of the Elements, published in *Nomenclature of Inorganic Chemistry: IUPAC Recommendations* 2005, Royal Society of Chemistry, 2005, ed. N. G. Connelly and T. Damhus. Also, any references to a Group or Groups of elements shall be to the Group or Groups reflected in this Periodic Table of the Elements using the IUPAC system for numbering groups.

All percentages, preferred amounts or measurements, ranges and endpoints thereof herein are inclusive, that is, "less than about 10" includes about 10. "At least" is equivalent to "greater than or equal to," and "at most" is, thus, equivalent "to less than or equal to." Numbers herein have no more precision than stated. Thus, "115" includes at least from 114.6 to 115.49. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageous" is used to denote a degree of preference more than required, but less than is denoted by the term "preferably."

Except in the examples or where otherwise indicated, all numbers expressing quantities, percentages, properties, functionalities and so forth in the specification are to be understood as being modified in all instances by the term "about." Those skilled in the art recognize that acceptable limits vary with equipment, conditions, applications, and other variables, but are determinable without undue experimentation in each situation where they are applicable. In some instances, variation or deviation in one parameter is acceptable to achieve another desirable end.

In the detailed description that follows, several chemical terms may be used, which for clarity are defined herein. Where a range in number of carbon atoms is set forth, e.g., $C_1$-$C_{20}$, the definition provides these numbers as a preferred general range; however, in the specific formulas described hereinafter, the range on number of carbon atoms for any particular class of radicals, e.g., "alkyl" or "aryl," may be more narrowly defined.

The term "comprising" is synonymous with "including," "containing," or "characterized by," is inclusive or open-ended, and does not exclude additional, unrecited elements, material, or steps. The term "consisting essentially of" indicates that in addition to specified elements, materials, or steps, unrecited elements, materials or steps are optionally present in amounts that do not unacceptably materially affect at least one basic and novel characteristic of the subject matter. The term "consisting of" indicates that only stated elements, materials, or steps are present, except that unrecited elements, materials or steps are optionally present to an extent that has no appreciable effect or are substantially absent.

The term "hydrocarbyl" refers to univalent organic radicals comprised of carbon and hydrogen atoms and, unless otherwise stated, containing from 1 to about 20 carbon atoms; including linear, branched, cyclic, saturated and unsaturated species, such as alkyl, alicyclic, alkenyl, aryl, alkaryl, and aralkyl groups. The term "substituted hydrocarbyl" refers to a hydrocarbyl radical that is substituted with one or more substituents disclosed hereinafter.

The term "hydrocarbylene" refers to a divalent hydrocarbyl radical.

The term "aryl" refers to a monovalent aromatic radical containing a single aromatic ring or containing multiple aromatic rings that are fused together or directly linked, or indirectly linked (such that different aromatic groups are bound through a common group, such as methylene or ethylene). Preferred aryl radicals contain one aromatic ring, for example, phenyl, and preferably, unless otherwise stated, from about 6 to about 20 carbon atoms. Closed-ring aromatic or aryl structures contain conjugated carbon-carbon double bonds characterized by $(4\delta+2)$ π-electrons, where $\delta$ is an integer greater than or equal to 1.

The term "arylene" refers to a divalent aryl radical.

The term "alkaryl" refers to a monovalent aryl radical with one or more alkyl substituents. The term "alkarylene" refers to a divalent aryl radical with one or more alkyl substituents.

The term "aliphatic" refers to an organic compound characterized by a straight or branched chain structure that contains saturated carbon bonds and may also contain one or more unconjugated carbon-carbon double bonds. Aliphatic compounds include paraffins, in which all carbon bonds are saturated, and olefins, in which one or more unconjugated C=C double bonds are present. Preferably, unless otherwise stated, the aliphatic compound contains from 1 to about 20 carbon atoms. For the purposes of this invention, the term "aliphatic" also includes "alicyclic" compounds defined hereinafter.

The term "alicyclic" refers to an aliphatic organic compound containing a closed ring structure comprising saturated carbon bonds and optionally one or more unconjugated carbon-carbon double bonds. Preferably, unless otherwise stated, the alicyclic compound contains from 4 to about 8 carbon atoms. The alicyclic compound does not have aromatic character as defined hereinabove.

The term "alkyl" refers to a saturated monovalent hydrocarbyl radical, which may be linear, branched, or cyclic (alicyclic). If linear or branched, the radical typically contains, unless otherwise noted, from 1 to about 20 carbon atoms, for example, methyl, ethyl, propyl, isopropyl, butyl, iso-butyl, and tert-butyl. If cyclic (alicyclic), the radical contains from 4 to about 8, preferably, 5 to 7 carbon atoms, such as cyclobutyl, cyclopentyl, cyclohexyl, cycloheptyl, and cyclooctyl, exclusive of carbon-containing substituents.

The term "alkylene" as used herein refers to a linear, branched, or cyclic divalent alkyl radical.

The term "aralkyl" or "arylalkyl" refers to a monovalent alkyl radical substituted with at least one aryl radical. The term "aralkylene" refers to a divalent alkylene radical substituted with at least one aryl radical.

The term "arylalicyclic" refers to an alicyclic radical substituted with at least one aryl group. An example of an arylalicyclic radical is "phenylcyclohexyl" or "phenylcyclopentyl.".

As used herein, any and all of the terms "hydrocarbyl," "hydrocarbylene," "alkyl," "alkylene," "aryl," "arylene," "aliphatic," "alkaryl," "alkarylene," "aralkyl," "aralkylene," "alicyclic" and "arylalicyclic" are intended to include substituted variants thereof. The term "substituted" or the words "substituted variants thereof" generally refer to the replacement of at least one hydrogen atom that is bonded to a carbon atom, for example, an alkyl or aryl carbon atom, with a non-hydrogen moiety. Preferred substituents for this invention include hydroxy, alkyl, aryl, aralkyl, and alkaryl radicals, wherein the aforementioned organic radicals contains from 1 to about 8 carbon atoms.

The term "aliphatic mono-ol" refers to an aliphatic compound having one hydroxyl substituent, The term "aliphatic ester" refers to an aliphatic compound having at least one ester substituent (—C(O)OR) wherein R is a monovalent hydrocarbyl radical, preferably, $C_1$-$C_{20}$ alkyl or $C_6$-$C_{20}$ aryl.

The term "aliphatic carboxylic acid" refers to an aliphatic compound having at least one carboxylic acid substituent (—C(O)OH)).

The term "aliphatic hemiacetal" refers to an aliphatic compound having one of the following structures: $RHC(OH)_2$ or $RHC(OR')(OH)$, wherein R and R' are monovalent hydrocarbyl radicals, preferably, of 1 to 20 carbon atoms.

The term "aliphatic lactone" refers to an alicyclic compound having an ester functionality as part of the closed ring.

The term "phenol" refers to an organic compound containing an aromatic benzene ring in which one H atom has been replace by hydroxyl.

In any listing of the words "aliphatic mono-ols, esters, carboxylic acids, and hemiacetals," it is to be understood that the word "aliphatic" modifies each species in the list.

In a broad concept, this invention provides for a process of refining a crude $C_6$-$C_{16}$ aliphatic diol comprising distilling one or more times a crude $C_6$-$C_{16}$ aliphatic diol comprising, in addition to the diol, one or more impurities selected from phenols, aliphatic mono-ols, esters, carboxylic acids, and hemiacetals, in the presence of an alkali metal compound and/or an alkaline earth metal compound under distillation conditions sufficient to obtain a purified $C_6$-$C_{16}$ aliphatic diol.

In a preferred embodiment of this invention, the $C_6$-$C_{16}$ aliphatic diol comprises a $C_6$-$C_{16}$ aliphatic monocyclic diol, more preferably, a cis/trans isomeric mixture of 1,3- and 1,4-cyclohexanedimethanol.

In a preferred embodiment of this invention, the alkali metal compound comprises an alkali metal hydroxide; and the alkaline earth metal compound comprises an alkaline earth metal hydroxide. In a more preferred embodiment, the alkali metal compound comprises sodium hydroxide or potassium hydroxide.

The crude $C_6$-$C_{16}$ aliphatic diol comprises a total of 6 to 16 carbon atoms arranged in a straight-chain or branched structure or arranged in a closed-ring structure (alicyclic), preferably having one ring (monocyclic), wherein the structure further comprises two hydroxy substituents. As relates to straight-chain or branched structures, the term "aliphatic" as used herein refers to compounds wherein each carbon atom in the straight-chain or branched structure is saturated (i.e., bonded to 4 other atoms through single bonds), and optionally, wherein the straight or branched structure contains one or more isolated (i.e., unconjugated) olefinically-unsaturated carbon-carbon double bonds (C═C). As relates to ring systems, the term "aliphatic" or "alicyclic" as used herein refers to a closed ring system formed from saturated carbon atoms, and optionally, one or more isolated (i.e., unconjugated) carbon-carbon double bonds. The alicyclic structure is differentiated from single closed-ring aromatic or aryl structures containing conjugated carbon-carbon double bonds characterized by (4δ+2) π-electrons, where δ is an integer greater than or equal to 1. The two hydroxy substituents characterizing the $C_6$-$C_{16}$ aliphatic diol advantageously are attached each to a different carbon atom. The hydroxy substituents may be attached directly to carbon atoms in the backbone of the straight-chain or branched structure or attached directly to ring carbon atoms. More preferably, the hydroxy substituents are attached to alkyl radicals that are themselves attached to the backbone carbon atoms in the straight-chain, branched, or ring structure. For example, two "hydroxymethyl" substituents may be attached to a cyclohexane ring to provide the preferred $C_6$-$C_{16}$ aliphatic diol employed in this invention, namely, (cis,trans)-(1,3)(1,4)-cyclohexanedimethanol.

Preferably, the $C_6$-$C_{16}$ aliphatic diol comprises a $C_6$-$C_{16}$ monocyclic aliphatic diol represented by the following formula I:

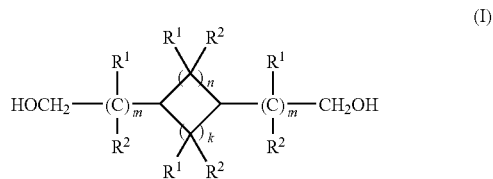

wherein each $R^1$ is independently selected from hydrogen, hydroxy, and $C_1$-$C_6$ monovalent hydrocarbyl radicals, for example, $C_1$-$C_6$ alkyl and phenyl, preferably, hydrogen and $C_1$-$C_3$ alkyl radicals; each $R^2$ is independently selected from hydrogen, hydroxy, and $C_1$-$C_6$ hydrocarbyl radicals, for example, $C_1$-$C_6$ alkyl and phenyl, preferably, hydrogen and $C_1$-$C_3$ alkyl radicals; n is an integer from 0 to 6, preferably, from 0 to 3, more preferably, 2; k is an integer from 0 to 6, preferably, from 0 to 3, more preferably, 2; n+k is greater than 2 and, more preferably, at most 6; and each m is independently an integer from 0 to about 3, preferably, 0 or 1. $R^1$ and $R^2$ may be substituted with one or more inert substituents that do not interfere with the process of this invention, non-limiting examples of which include hydroxy, alkyl, aryl aralkyl, and alkaryl radicals, wherein the aforementioned organic radicals preferably comprise from 1 to about 8 carbon atoms. Preferably, the inert substituent comprises hydroxy. In the aforementioned preferred formula (I), the selection of $R^1$, $R^2$, m, n, k, and inert substituents is limited to a total number of carbon atoms in the composition within the range from 6 to 16. It is further noted that if one of n or k is 0, then the two subgroups —$(CR_1R_2)_m$— are directly linked to each other forming a ring with the n subunits.

The $C_6$-$C_{16}$ aliphatic diol can be prepared by any convenient method described in the art. Preferably, the $C_6$-$C_{16}$ monocyclic aliphatic diol is prepared in a three-stage synthesis comprising: (1) reacting a diene with a dienophile comprising a formyl-substituted olefin in a Diels Alder addition or condensation reaction to prepare an olefinically-unsaturated monocyclic carboxaldehyde; (2) hydroformylating the olefinically-unsaturated monocyclic carboxaldehyde with carbon monoxide and hydrogen (syngas or synthesis gas) in the presence of a transition metal-organophosphite ligand complex catalyst to obtain a $C_6$-$C_{16}$ monocyclic aliphatic dicarboxaldehyde; and (3) hydrogenating the $C_6$-$C_{16}$ monocyclic aliphatic dicarboxaldehyde with hydrogen in the presence of a hydrogenation catalyst to obtain the crude $C_6$-$C_{16}$ monocyclic aliphatic diol. While such synthetic schemes are not the focus of the present invention, reference is nevertheless made to U.S. Pat. No. 6,252,121 for a description of suitable dienes, dienophiles, ligands, transition metals, transition metal-ligand complex hydroformylation catalysts, hydrogenation catalysts, and process conditions suitable for the above-described reaction scheme; the aforementioned US patent being incorporated herein by reference.

More preferably, with reference to U.S. Pat. No. 6,252,121, the $C_6$-$C_{16}$ aliphatic diol comprises a mixture of cis and trans isomers of 1,3- and 1,4-cyclohexanedimethanol ("cis/trans-(1,3)(1,4)-cyclohexanedimethanol"), obtained by reacting 1,3-butadiene with acrolein via a Diels Alder reaction to form 3-cyclohexene-1-carboxaldehyde; thereafter hydroformylating the 3-cyclohexene-1-carboxaldehyde with syngas in the presence of a rhodium-triorganophosphite ligand complex catalyst so as to prepare cis/trans-(1,3)(1,4)-cyclohexanedicarboxaldehyde, which is subsequently hydrogenated to a crude cis/trans-(1,3)(1,4)-cyclohexanedimethanol. Two of the four cyclohexanedimethanol isomers are depicted in Formulas IIa (1,3-isomer, shown as trans isomer, but may also exist as cis isomer) and IIb (1,4-isomer, shown as cis isomer, but may also exist as trans isomer) respectively:

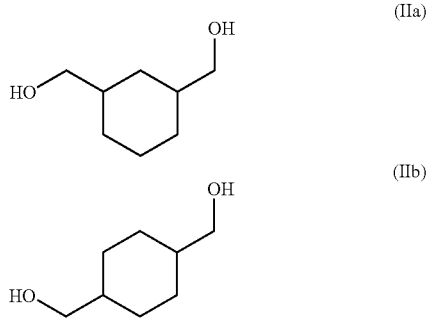

Advantageously, the aforementioned isomeric composition comprises from about 50 to 60 percent by weight of the 1,3-isomer and from about 40 to 50 percent by weight of the 1,4-isomer.

The one or more impurity mono-ols, esters, and carboxylic acids are not limited to any particular structure, although they are generally aliphatic in nature inasmuch as they are derived from the aliphatic compounds used to prepare the aliphatic diol. Of course, the aliphatic mono-ol will have only one hydroxyl (—OH) substituent. As noted hereinbefore, the impurity aliphatic mono-ols can arise from hydrogenation of a saturated or unsaturated mono-aldehyde intermediate in the synthesis of the $C_6$-$C_{16}$ diol. Impurity esters and carboxylic acids are characterized by —C(O)OR and —C(O)OH functionality, respectively, wherein R is generically any monovalent hydrocarbyl radical, advantageously, a $C_{1-20}$ alkyl radical or a $C_{6-20}$ aryl radical. Impurity carboxylic acids can arise from oxidation of the product aldehydes that are precursors to the diol. Impurity esters can arise from condensation of any mono-ol or diol with the acid. Lactones are a special class of impurity esters, being characterized as cyclic esters that arise from intra-molecular condensation of an intermediate compound or heavy containing both acid and alcohol functionalities. Hemiacetals are characterized as hydrated aldehydes, RHC(OH)$_2$ or RHC(OR')(OH), wherein R and R' each represent a monovalent hydrocarbyl radical as noted hereinabove. Hemiacetals can arise from hydrolysis of aldehyde products during hydroformylation or simple condensation of an alcohol with an aldehyde (such as during hydrogenation). In contrast, impurity phenols are characterized as hydroxy-substituted aromatic compounds, the most likely source of which is hydrolysis of the organophosphite ligand(s) used in the hydroformylation catalyst.

The $C_6$-$C_{16}$ aliphatic diol and the impurity mono-ol(s), ester(s), carboxylic acid(s), hemiacetals(s), and phenol(s) in the crude diol or at any stage of purification can be identified by conventional analytical methods known to the skilled person, including but not limited to infrared (IR) spectroscopy, $^1$H and $^{13}$C nuclear magnetic resonance spectroscopy (NMR), gas phase chromatography, and mass spectroscopy. American Society for Testing and Materials standard test method ASTM D 1613-96 (ASTM, Conshohocken, Pa., 1996, reapproved 1999), incorporated herein by reference, is suitably employed for the determination of total acidity of the diol. (ASTM D 1613-96 reports the acidity in mg KOH per gram sample, which can be converted to equivalents acid per gram sample by dividing by 56,100.) Standard test method ASTM D 1209-00 (ASTM, West Conshohocken, 2000), incorporated herein by reference, is suitably employed to evaluate the color of the crude diol or any stage of purification thereof.

Other impurity components may be present in the crude $C_6$-$C_{16}$ aliphatic diol including, for example, water, one or more $C_1$-$C_8$ alcohols, such as methanol, ethanol, isopropanol, butanol, and the like; one or more $C_5$-$C_{10}$ alkanes, such as pentane, hexane, cyclohexane, n-heptane, octane, and the like; dialdehydes that are precursors to the diol, as well as other unidentified lights, intermediates, and heavies. For the purposes of this invention, the term "lights" refers to compounds that are generally structurally different from the diol (e.g., solvents, volatiles) and that have a normal boiling point more than 50° C. lower than the normal boiling point of the diol. As used herein, the term "intermediates" refers to compounds that are structurally similar but not identical to the diol, particularly, hydroxy-substituted compounds including, for example, mono-ols, enols, phenols and other like but unidentified decomposition materials, which have a normal boiling point lower than the normal boiling point of the diol. As used herein, the term "heavies" refers to compounds that have a normal boiling point higher than the normal boiling point of the diol; examples of heavies include dimers, trimers, and various esters. Referring to the diol, the term "normal boiling point" is defined herein as the temperature at which the liquid and gaseous phases of the diol exist in equilibrium at a diol vapor pressure of 1 atmosphere (101 kPa).

The concentration of each impurity in the crude diol will vary depending upon the particular $C_6$-$C_{16}$ aliphatic diol under consideration and its method of preparation. Preferably, the crude $C_6$-$C_{16}$ aliphatic diol comprises from about 60 to about 80 weight percent $C_6$-$C_{16}$ diol product and one or more of the following impurities in the following percentages by weight:

| | |
|---|---|
| Mono-ols | about 0.5 to 10 percent |
| Esters | about 1 to 5 percent |
| Carboxylic acids | about 0.5 to 10 percent |
| Hemiacetals/Lactones | about 1 to 5 percent |
| Phenols | about less than 1 percent |
| Lights | about 15 to 25 percent |
| Intermediates* | about 0.1 to 5 percent |
| (*other than mono-ols, hemiacetals/lactones) | |
| Heavies | about 0.1 to 5 percent |

Optionally, dialdehydes can also be present in a quantity less than about 0.1 weight percent.

More preferably, the $C_6$-$C_{16}$ diol comprises from about 60 to about 80 weight percent cis/trans-(1,3)(1,4)-cyclohexanedimethanol and one or more of the following impurities in the following typical percentages, by weight:

| | |
|---|---|
| Cyclohexanemethanol | about 0.5 to 5 percent |
| Cyclohexenemethanol | about 0.5 to 5 percent |
| Esters | about 0.1 to 5 percent |
| Carboxylic acids | about 0.5 to 10 percent |
| Hemiacetals/Lactones | about 1 to 5 percent |
| Phenols | about less than 1 percent |
| Lights | about 15 to 25 percent |
| Intermediates* | about 0.1 to 5 percent |
| (*other than mono-ols, hemiacetals/lactones) | |
| Heavies | about 0.1 to 5 percent |

The refining process of this invention requires the presence of an alkali metal compound and/or an alkaline earth metal compound to effect an improved separation of purified $C_6$-$C_{16}$ aliphatic diol product. While this invention should not be limited or bound to any theory presented herein, it is believed that the alkali and/or alkaline earth metal compound neutralizes acids, including carboxylic and other acids, which may be present or which may form during distillation and which catalyze the formation of hemiacetals. In the presence of alkali and/or alkaline earth metal compound, the formation and decomposition of hemiacetals is believed to be inhibited or blocked altogether. Moreover, the alkali and/or alkaline earth metal compound is believed to be capable of converting phenols to non-volatile alkali or alkaline earth metal salts Likewise, lactones are believed to be converted to non-volatile alkali or alkaline earth metal salts of hydroxyacids. Surprisingly, however, the presence of the alkali metal compound and/or alkaline earth metal compound does not catalyze undesirable side-reactions of the product $C_6$-$C_{16}$ diol.

The alkali metal compounds employable in the present invention include all such inorganic and organic alkali compounds and salts having a capacity to neutralize the acidity of the crude diol, the alkali metal comprising the Group 1 metals of the Periodic Table of the Elements, including particularly lithium, sodium, potassium, and cesium. Non-limiting examples of suitable alkali metal compounds include sodium hydroxide, potassium hydroxide, cesium hydroxide, lithium hydroxide, sodium hydrogen carbonate, sodium carbonate, potassium carbonate, cesium carbonate, lithium carbonate, sodium acetate, potassium acetate, cesium acetate, lithium acetate, sodium stearate, potassium stearate, cesium stearate, lithium stearate, sodium borohydride, sodium phenylborate, sodium benzoate, potassium benzoate, cesium benzoate, lithium benzoate, disodium hydrogen phosphate, dipotassium hydrogen phosphate, dilithium hydrogen phosphate, disodium phenylphosphate, disodium salt of bisphenol A, dipotassium salt of bisphenol A, dicesium salt of bisphenol A, dilithium salt of bisphenol A, sodium phenolate, potassium phenolate, cesium phenolate, lithium phenolate, and mixtures thereof. Preferred species include the alkali metal hydroxides, more preferably, sodium hydroxide or potassium hydroxide, and mixtures thereof.

The alkaline earth metal compound employable in the present invention include all such inorganic and organic alkaline earth compounds and salts having a capacity to neutralize the acidity of the crude diol, the alkaline earth metals comprising those of Group 2 of the Periodic Table of the Elements including particularly beryllium, magnesium, calcium, strontium, and barium. Non-limiting examples of suitable alkaline earth metal compounds include magnesium hydroxide, calcium hydroxide, strontium hydroxide, barium hydroxide, magnesium hydrogen carbonate, calcium hydrogen carbonate, strontium hydrogen carbonate, barium hydrogen carbonate, magnesium acetate, calcium acetate, strontium acetate, barium acetate, magnesium stearate, calcium stearate, calcium benzoate, and magnesium phenylphosphate, and mixtures thereof. Preferred species include one or a mixture of alkaline earth metal hydroxides.

The alkali metal compounds and alkaline earth metal compounds can be used alone or in a combination of two or more such compounds, in the form of solid(s) or in solution in water or a $C_1$-$C_6$ alkanol, more preferably, methanol or ethanol, or a mixture of alkanol(s) and/or water. The concentration of the solution is not particularly critical. Any concentration of alkali metal compound and/or alkaline earth metal compound can be used up to its solubility limit in water, or the alkanol, or mixture thereof. Preferably, the concentration ranges from about 1 to about 55 weight percent, based on the total weight of the solvent(s) and alkali metal and/or alkaline earth metal compound(s).

The total quantity of alkali metal compound and/or alkaline earth metal compound used in the process of this invention advantageously is greater than about 0.8 equivalent, preferably, greater than about 1.0 equivalent, and more preferably, greater than about 1.2 equivalents, per equivalent of acid in the diol. Advantageously, the total quantity of alkali metal compound and/or alkaline earth metal compound is less than about 2.5, preferably, less than about 2.0, and more preferably, less than about 1.8 equivalents, per equivalent of acid in the diol. In one most preferred embodiment, an excess of alkali and/or alkaline earth metal compound is employed, namely, greater than 1.25 equivalents, up to 2.50 equivalents, per equivalent of acid in the diol, for the purpose of neutralizing any acidity additionally formed by contact of aldehydes present in the diol with oxygen. The amount of alkali metal compound and/or alkaline earth metal compound advantageously is greater than about 100 parts per million (ppm), preferably, greater than about 500 ppm, in total, based on the weight of the crude $C_6$-$C_{16}$ diol. The amount of alkali metal compound and/or alkaline earth metal compound advantageously is less than about 5,000 ppm, and preferably, less than about 2,000 ppm, in total, based on the weight of the crude $C_6$-$C_{16}$ diol.

As a general practice, the alkali metal compound and/or alkaline earth metal compound, either as a solid(s) or an aqueous or alcohol solution, is dissolved in the crude $C_6$-$C_{16}$ aliphatic diol. The dissolution procedure is conventional and can involve any convenient form of addition and mixing known to the skilled person. Thereafter, the crude $C_6$-$C_{16}$ diol is fed to a first distillation column and subjected to distillation to remove substantially lights including water, alkanes, and other volatiles and low boiling components, so as to recover a partially-purified $C_6$-$C_{16}$ diol having from about 90 to 95 percent purity. The first distillation to remove lights is conventional in design. A column is employed that is not necessarily staged or packed. A simple reflux condenser advantageously is used. A temperature below the normal boiling point of the diol is applied as needed to remove the low boiling components. For the preferred purification of a $C_6$-$C_{16}$ aliphatic monocyclic diol, more preferably cis/trans-(1,3)(1,4)-cyclohexanedimethanol, the temperature of this first distillation preferably ranges from about 80° C. to about 210° C. at the bottom of the column and from about 20° C. to about 120° C. at the top (head) of the column. The first distillation advantageously is conducted at about 1 atmosphere (101 kPa) or slightly higher pressures at about 1 to 2 psig over-pressures (6.9-13.8 kPa). The low boiling components are recovered as an overhead or top stream. Since the overhead advantageously contains both water and organics having low water solubility, two substantially-immiscible liquid phases are likely to be recovered. The bottom stream from the first distillation column contains only a partially-purified diol comprising one or more impurity aliphatic mono-ols, esters (including lactones), carboxylic acids, hemiacetals, and/or phenols. The concentration of each impurity in the partially-purified $C_6$-$C_{16}$ diol advantageously ranges from greater than about 0.01 to less than about 2 weight percent, preferably, from about 0.1 to about 1.0 weight percent, based on the total weight of the partially-purified diol.

Thereafter, the bottoms stream from the first distillation column is fed to a second distillation column and distilled under conditions sufficient to separate and recover a purified $C_6$-$C_{16}$ aliphatic diol. The distillation conditions in the second column generally vary depending upon the specific $C_6$-$C_{16}$ diol to be purified, its normal boiling point, and the types and quantities of impurities to be removed. The second distillation column advantageously comprises from about 30 to about 100 theoretical trays. The column can be packed with a suitable packing, including for example, glass beads, stainless steel mesh, ceramics in any form, such as saddles, and like conventional materials. The second distillation column advantageously is operated at a sub-atmospheric pressure suitably ranging from about 15 torr (2.0 kPa) to about 50 torr (6.7 kPa). A reflux ratio ranging from about 1:10 to about 10:1 is suitably employed. In the preferred distillation of a $C_6$-$C_{16}$ aliphatic monocyclic diol, more preferably cis/trans-(1,3)(1, 4)-cyclohexanedimethanol, the bottom temperature of the column advantageously ranges from about 165° C. to about 250° C., while the head temperature advantageously ranges from about 160° C. to about 180° C. The impurities are taken as a head stream; whereas the $C_6$-$C_{16}$ diol is taken as bottom stream, which also typically contains heavies.

The heavies can be removed in a conventional finishing distillation based upon the boiling point of the diol to yield the $C_6$-$C_{16}$ aliphatic diol in purified form as an overhead stream. A preferred process removes the lower boiling impurities, as noted above, and then recycles the bottoms to the same column for the finishing distillation. This preferred method is possible when essentially no additional impurities are being generated during distillation, as per the invention described herein.

Each distillation described hereinabove may be conducted in batch or continuous mode. Preferably, on a commercial scale, a continuous mode of operation is employed wherein a feed comprising crude diol and the desired quantity of alkali and/or alkaline earth metal compound is continuously fed to a sequence of distillation columns with a recycle to any particular column as desired.

The thusly-separated and purified $C_6$-$C_{16}$ aliphatic diol advantageously comprises the following composition based on weight percentages:

| | |
|---|---|
| $C_6$-$C_{16}$ Diol | greater than 99 percent |
| Mono-ols | less than 0.1 percent |
| Esters | less than 0.1 percent |
| Carboxylic acids | less than 0.1 percent |
| Hemiacetals/Lactones | less than 0.1 percent |
| Phenols | less than 0.1 percent |
| Lights | less than 0.1 percent |
| Intermediates* | less than 0.1 percent |
| (*other than mono-ols and hemiacetals/lactones) | |
| Heavies | less than 0.1 percent |
| Dialdehydes | less than 0.1 percent |

When the subject invention is conducted as described hereinabove, a purer form of the $C_6$-$C_{16}$ diol is recovered at each distillation stage in a yield greater than about 90 percent, preferably, greater than about 95 percent, and more preferably, greater than about 98 percent, by weight, based on the weight of the diol fed to the particular distillation stage, as determined advantageously by a calibrated gas chromatography analysis (GC). It is noted that GC analysis usually cannot determine the quantity of heavies present. The heavies are usually calculated as the difference in weight between the weight of the sample analyzed and the total weight of the diol and other impurities determined by GC to be present in the sample. Any standard GC column that separates components of a mixture based on differences in boiling points can be employed for the analysis.

The purified $C_6$-$C_{16}$ aliphatic diol recovered from the final distillation desirably exhibits a total acidity of less than about 500 parts per million (ppm) or less than about 0.05 weight percent, calculated as acetic acid, based on the weight of the diol product and as measured by test method ASTM D 1613-96. Moreover, based on test method ASTM D 1209-00, the color of the purified $C_6$-$C_{16}$ aliphatic diol advantageously is rated less than about 10 (numbers of 7 or less being more desirable).

The following examples are set forth to illustrate the invention. The examples should not be construed to limit the invention in any manner. Unless otherwise noted, all percentages are given in units of weight percent.

Comparative Experiment 1

A sample of crude $C_6$-$C_{16}$ diol comprising a mixture of cis/trans-(1,3)(1,4)-cyclohexanedimethanol is purified via three staged distillations. The crude $C_6$-$C_{16}$ diol is prepared by the synthesis scheme set forth in U.S. Pat. No. 6,252,121, by reacting butadiene with acrolein in a Diels Alder addition reaction to form 3-cyclohexene-1-carboxaldehyde; hydroformylating 3-cyclohexene-1-carboxaldehyde with carbon monoxide and hydrogen in the presence of a rhodium-triorganophosphite ligand complex catalyst to prepare cis/trans-(1,3)(1,4)-cyclohexane-dicarboxaldehyde, which is then hydrogenated in the presence of a nickel catalyst to the crude aliphatic diol having the following composition as determined by gas chromatography: diol (75.24 percent), water (19.40 percent), isopropanol (0.51 percent), n-heptane (1.00 percent), cyclohexanemethanol (1.99 percent), intermediates including alkylated phenols (0.29 percent), dialdehydes and lactones (0.10 percent), hemiacetals (0.98 percent). Heavies are not detectable. The acidity is 0.51 percent, as determined by ASTM D 1613-96. The first distillation stage consists of an atmospheric distillation to remove volatiles and lights. A bottoms stream from the first distillation column is subjected to a second distillation at elevated temperature and reduced pressure to remove additional lower boiling impurities. Bottoms from the second distillation column are subjected to a third distillation at elevated temperature and reduced pressure to remove heavies and to obtain in an overhead stream a purified diol product. Distillation conditions of each column are noted in Table 1. Each column contains 15 theoretical trays and operates at a reflux ratio of 1:10. It is noted that no alkali metal compound or alkaline earth metal compound is employed in the distillations.

TABLE 1

| | | First Distillation | | | Second Distillation | | Final Distillation | |
|---|---|---|---|---|---|---|---|---|
| | Initial feed | | | | | | | |
| Head Temperature ° C. | | 100 | @760 mm Hg (101 kPa) | | 115-192 | @35 mmHg (4.7 kPa) | 192 | @35 mm Hg (4.7 kPa) |
| Pot Temperature ° C. | | 175 | @760 mm Hg (101 kPa) | | 195-200 | | 202-220 | |
| Composition | wt % | Head Aqueous | Head Organic | Bottom | Head | Bottom | Head | Bottom |
| Water | 19.4 | 95.4 | 2.9 | 1 | 0.66 | 0.02 | 0.018 | n/a |
| Isopropanol | 0.51 | 1.18 | 1.75 | — | — | — | — | n/a |
| n-Heptane | 1.0 | 0.23 | 32.83 | — | — | — | — | n/a |
| Cyclohexanemethanol | 1.99 | 1.04 | 48.06 | 1.09 | 9.27 | — | — | n/a |
| Intermediates | 0.29 | 0.16 | 9.14 | 0.24 | 0.661 | 0.012 | 0.032 | n/a |
| Dialdehydes + Lactones * | 0.1 | 0.42 | 0.44 | 0.64 | 5.287 | 0.024 | 0.006 | n/a |
| Hemiacetals* | 0.98 | 0.07 | 0.36 | 1.46 | 8.862 | 0.029 | 0.032 | n/a |
| Cis/trans-(1,3)(1,4) Cyclohexanedimethanol | 75.24 | 1.5 | 4.52 | 95.57 | 75.92 | 99.935 | 99.93 | n/a |
| Heavies | Non-detectable | | | | | | | |
| Acidity, % as HAc | 0.51 | 0.06 | 0.02 | 0.44 | 0.024 | n/a | 0.44 | n/a |
| Yields, wt % | | 19.1 | 2.3 | 78.6 | 9.9 | 90.1 | 94.3 | 5.7 |
| Color, APHA | | | | | | | 7 | Brown |

It is seen from Table 1 that during each distillation, the quantities of certain impurities increase as compared with the crude diol feed. This result implies that the distillations themselves produce impurities, thereby rendering it necessary to use three columns to achieve a purified diol product. More specifically, at only 100° C. in the first column, the formation of impurities during distillation is evident. The species identified as dialdehydes and lactones dramatically increase in every fraction, and clearly more are present after distillation as compared with the diol feed. While dialdehydes present in the crude diol can be readily removed by distillation without any special treatment or consideration, the production of added dialdehydes during distillation, presumably from splitting of intermediates and heavies impurities, presents a problem for obtaining purified product.

From Table 1 other impurities are also seen to increase including cyclohexanemethanol, hemiacetals, and intermediates including alkylated phenols. A relatively high level of diol in the overhead stream from the second distillation column is needed to remove the increased impurities, but results in an efficiency loss of desired diol product. Even after the third distillation, the acidity of the diol product, resulting presumably from cyclohexanecarboxylic acid, is unacceptably high. Overall diol recovery after the three steps is only 81 weight percent. Moreover, the total acidity of the recovered diol is 0.44 percent (or 4400 ppm). Color is rated 7, per test method ASTM D 1209-00. The results indicate that further distillation is needed in order to reduce the acidity to commercially acceptable levels.

Example 1

A sample of a crude $C_6$-$C_{16}$ diol comprising a mixture of cis/trans-(1,3)(1,4)-cyclohexanedimethanol, prepared in a manner similar to that described in Comparative Experiment 1, is treated with aqueous potassium hydroxide. The crude diol comprises the aforementioned cyclohexanedimethanol (74.02 percent), water (3.8 percent), isopropanol (12.64 percent), n-heptane (2.31 percent), lights (2.88 percent), cyclohexanemethanol (1.15 percent), 3-cyclohexene-1-methanol (0.28 percent), dialdehydes (0.03 percent), 1,3-hemiacetals (1.16 percent), intermediates (1.05 percent), and heavies (0.68 percent). The acidity of the crude diol is 0.129 percent (0.021 equivalents/g), as determined by test method ASTM D 1613-96. The quantity of potassium hydroxide employed is 1.5 equivalents per acid equivalent of the diol sample. The crude diol with added potassium hydroxide is then subjected to lights removal. The lights are distilled out at atmospheric pressure. Thereafter, the bottoms from the lights removal column are fed to a first distillation column and distilled at elevated temperature and reduced pressure. Distillation conditions and results are set forth in Table 2. In the second distillation, two small head cuts (#1 and #2) are taken before taking the main overhead cut. The bottoms from the second distillation column are recycled to the column and re-distilled in a finishing step to collect an overhead stream of a purified cis/trans-(1,3)(1,4)-cyclohexandimethanol, as shown in Table 2.

Example 1 (Distillation with added KOH)

|  | Initial Feed | Lights removal | | First Distillation | | Final Distillation | | | Overhead Product |
|---|---|---|---|---|---|---|---|---|---|
|  |  | Demister | Heads | Overhead | Bottom | Head #1 | Head #2 | Bottom | |
| Head Temperature ° C. |  | 22-110 | | 168-170 | | 170-172 | | | |
| Pot temperature ° C. |  | 86-205 | | 168-180 | | 172-180 | | | |
| Pressure mmHg |  | 775-760 (103-101 kPa) | | 20 (2.7 kPa) | | 20 (2.7 kPa) | | | |
| Color (APHA) | 7 | 7 | 3 | 9 | Brown | 120 | 48 | Brown | 7 |
| Acidity (wt. % as Acetic Acid) | 0.129 | 0.0004 | 0.0009 | 0.0033 | N/A | 0.315 | 0.0121 | N/A | 0.0017 |
| Water | 3.8 | 15.58 | 27.69 | 0.01 | 0 | 0.02 | 0.01 | 0 | 0.01 |
| Isopropanol | 12.64 | 61.48 | 68.96 | 0 | 0 | 0 | 0 | 0 | 0 |
| n-Heptane | 2.31 | 9.32 | 0.01 | 0 | 0 | 0 | 0 | 0 | 0 |
| Lights | 2.88 | 13.2 | 0.34 | 0.02 | 0 | 0.3 | 0 | 0 | 0.03 |
| Cyclohexanemethanol | 1.15 | 0.28 | 2.1 | 0.72 | 0.05 | 53.1 | 0.56 | 0 | 0 |
| 3-Cyclohexene-1-methanol | 0.28 | 0.07 | 0.34 | 0.17 | 0 | 13.29 | 0.17 | 0 | 0 |
| Dialdehydes | 0.03 | 0 | 0 | 0.01 | 0 | 0.6 | 1.24 | 0.06 | 0 |
| 1,3-Hemiacetal | 1.16 | 0 | 0.04 | 1.04 | 0.07 | 21.79 | 26.93 | 0.06 | 0.02 |
| Cis/trans-(1,3)(1,4)cyclohexane dimethanol | 74.02 | 0 | 0 | 97.74 | 56.18 | 0 | 67.88 | 34.87 | 99.85 |
| Intermediates | 1.05 | 0.07 | 0.52 | 0.29 | 4.61 | 10.9 | 3.21 | 4.84 | 0.09 |
| Heavies | 0.68 | 0 | 0 | 0 | 39.09 | 0 | 0 | 60.17 | 0 |
| % Yield |  | 19 | 1 | 74 | 3 | 2 | 6 | 1 | 89 |

It is observed from Table 2 that during this first distillation no additional impurities are formed, in contrast to Comparative Experiment 1 hereinabove. The dialdehydes, hemiacetals, and intermediates do not increase upon the stress of distillation; and consequently, a second Lights distillation step is avoided. The overall recovery of purified diol product from the two distillations is 87 percent, which is superior to the aforementioned comparative experiment. The final acidity level of the purified diol product is low at only 0.0033 percent (33 ppm), and therefore is superior to the diol product recovered in the comparative experiment. The color of the purified diol product is rated 7, per test method ASTM D 1209-00, and therefore comparable to the diol product recovered in the comparative experiment, which however took one further distillation to achieve.

Embodiments of the Invention include the following:

1. A process of refining a crude $C_6$-$C_{16}$ aliphatic diol comprising distilling one or more times a crude $C_6$-$C_{16}$ aliphatic diol comprising, in addition to the diol, one or more impurities selected from phenols and aliphatic mono-ols, esters, carboxylic acids, and hemiacetals, and mixtures thereof, in the presence of an alkali metal compound and/or an alkaline earth metal compound under distillation conditions sufficient to obtain a purified $C_6$-$C_{16}$ aliphatic diol.

2. A process of any other embodiment wherein the $C_6$-$C_{16}$ aliphatic diol comprises a $C_6$-$C_{16}$ monocyclic aliphatic diol represented by the following formula:

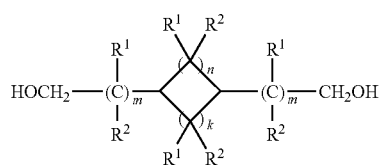

wherein each W is independently selected from hydrogen, hydroxy, and $C_1$-$L_6$ monovalent hydrocarbyl radicals, preferably, hydrogen and $C_1$-$C_3$ alkyl radicals; each $R^2$ is independently selected from hydrogen, hydroxy, and $C_1$-$C_6$ hydrocarbyl radicals, preferably, hydrogen and $C_1$-$C_3$ alkyl radicals; n is an integer from 0 to 6, preferably, from 0 to 3, more preferably, 2; k is an integer from 0 to 6, preferably, from 0 to 3, more preferably, 2; n+k is greater than 2 and, more preferably, at most 6; and each m is independently an integer from 0 to about 3, preferably, 0 or 1; and optionally wherein $R^1$ and $R^2$ may be substituted with one or more inert substituents including hydroxy, alkyl, aryl aralkyl, and alkaryl radicals, the aforementioned organic radicals preferably comprising from 1 to about 8 carbon atoms.

3. A process of any other embodiment wherein the crude $C_6$-$C_{16}$ aliphatic diol comprises from about 60 to about 80 weight percent $C_6$-$C_{16}$ aliphatic diol and one or more of the following impurities in the following percentages by weight:

| | |
|---|---|
| Mono-ols | 0.5 to 10 percent |
| Esters | 1 to 5 percent |
| Carboxylic acids | 0.5 to 10 percent |
| Hemiacetals/Lactones | 1 to 5 percent |
| Phenols | less than 1 percent |
| Lights | 15 to 25 percent |
| Intermediates* | 0.1 to 5 percent |
| (*other than mono-ols, hemiacetals and lactones) | |
| Heavies | 0.1 to 5 percent |

4. A process of any other embodiment wherein the crude $C_6$-$C_{16}$ aliphatic diol comprises cis/trans-(1,3)(1,4)-cyclohexanedimethanol.

5. A process of any other embodiment wherein the crude $C_6$-$C_{16}$ aliphatic diol comprises from about 60 to about 80 weight percent cis/trans-(1,3)(1,4)-cyclohexanedimethanol and one or more of the following impurities in the following typical percentages, by weight:

| | |
|---|---|
| Cyclohexanemethanol | about 0.5 to 5 percent |
| Cyclohexenemethanol | about 0.5 to 5 percent |
| Esters | about 0.1 to 5 percent |
| Carboxylic acids | about 0.5 to 10 percent |
| Hemiacetals/Lactones | about 1 to 5 percent |
| Phenols | about less than 1 percent |
| Lights | about 15 to 25 percent |
| Intermediates* | about 0.1 to 5 percent |
| (*other than mono-ols, hemiacetals/lactones) | |
| Heavies | about 0.1 to 5 percent |

6. A process of any other embodiment wherein the alkali metal compound is selected from the group consisting of sodium hydroxide, potassium hydroxide, cesium hydroxide, lithium hydroxide, sodium hydrogen carbonate, sodium carbonate, potassium carbonate, cesium carbonate, lithium carbonate, sodium acetate, potassium acetate, cesium acetate, lithium acetate, sodium stearate, potassium stearate, cesium stearate, lithium stearate, sodium borohydride, sodium phenylborate, sodium benzoate, potassium benzoate, cesium benzoate, lithium benzoate, disodium hydrogen phosphate, dipotassium hydrogen phosphate, dilithium hydrogen phosphate, disodium phenylphosphate, disodium salt of bisphenol A, dipotassium salt of bisphenol A, dicesium salt of bisphenol A, dilithium salt of bisphenol A, sodium phenolate, potassium phenolate, cesium phenolate, lithium phenolate, and mixtures thereof.

7. A process of any other embodiment wherein the alkaline earth metal compound is selected from the group consisting of magnesium hydroxide, calcium hydroxide, strontium hydroxide, barium hydroxide, magnesium hydrogen carbonate, calcium hydrogen carbonate, strontium hydrogen carbonate, barium hydrogen carbonate, magnesium acetate, calcium acetate, strontium acetate, barium acetate, magnesium stearate, calcium stearate, calcium benzoate, and magnesium phenylphosphate, and mixtures thereof.

8. A process of any other embodiment wherein the alkali metal compound comprises an alkali metal hydroxide and wherein the alkaline earth metal compound comprises an alkaline earth metal hydroxide.

9. A process of any other embodiment wherein the quantity of alkali metal compound and/or alkaline earth metal compound is greater than 0.8, preferably greater than 1.0, and more preferably, greater than 1.2, and less than 2.5, preferably less than 2.0, and more preferably less than 1.8 equivalents per equivalent of acid in the diol.

10. A process of any other embodiment wherein the quantity of alkali metal compound and/or alkaline earth metal compound is greater than 1.25 and less than 2.50 equivalents per equivalent of acid in the diol.

11. A process of any other embodiment wherein the amount of alkali metal compound and/or alkaline earth metal compound is greater than 100 parts per million (ppm), preferably greater than 500 ppm, and less than 5,000 ppm, preferably less than 2,000 ppm, in total, based on the weight of the crude $C_6$-$C_{16}$ diol.

12. A process of any other embodiment wherein a first distillation is conducted in a distillation column to remove lights at a bottom temperature from 80° C. to 210° C. and a top temperature from 20° C. to 120° C. and at about 1 atmosphere (101 kPa) pressure, optionally, with 1-2 psig overpressures (6.9-13.8 kPa).

13. A process of any other embodiment wherein a second distillation is conducted in a distillation column at a bottom temperature ranging from 165° C. to 250° C. and a top temperature ranging from 160° C. to 180° C. at a sub-atmospheric pressure ranging from 15 torr (2.0 kPa) to 50 torr (6.7 kPa).

14. A process of any other embodiment wherein a second distillation is conducted in a distillation column comprising from 30 to 100 theoretical trays.

15. A process of any other embodiment wherein a second distillation is conducted at a reflux ratio ranging from 1:10 to 10:1.

16. A process of any other embodiment wherein the one or more distillations are conducted in a continuous mode of operation.

17. A process of any other embodiment wherein the purified $C_6$-$C_{16}$ aliphatic diol is recovered at each distillation stage in a yield of greater than 90 percent, preferably greater than 95 percent, and more preferably, greater than 98 percent by weight, based on the weight of the diol fed to the particular distillation stage.

18. A process of any other embodiment wherein the purified $C_6$-$C_{16}$ aliphatic diol comprises the following composition based on weight percentages:

| | |
|---|---|
| $C_6$-$C_{16}$ Diol | greater than 99 percent |
| Mono-ols | less than 0.1 percent |
| Esters | less than 0.1 percent |
| Carboxylic acids | less than 0.1 percent |
| Hemiacetals/Lactones | less than 0.1 percent |
| Phenols | less than 0.1 percent |
| Lights | less than 0.1 percent |
| Intermediates* | less than 0.1 percent |
| (*other than mono-ols and hemiacetals/lactones) | |
| Heavies | less than 0.1 percent |
| Dialdehydes | less than 0.1 percent |

19. A process of any other embodiment wherein the purified $C_6$-$C_{16}$ aliphatic diol has a color rated less than 10, preferably 7 or less, per test method ASTM D 1209-00.

20. A process of any other embodiment wherein the purified $C_6$-$C_{16}$ aliphatic diol has a total acidity of less than 500 parts per million, calculated as acetic acid, and based on the weight of the diol.

21. A process of any other embodiment wherein the $C_6$-$C_{16}$ aliphatic diol comprises cis/trans-(1,3)(1,4)-cyclohexanedimethanol, and wherein the alkali metal compound comprises potassium hydroxide.

The invention claimed is:

1. A process of refining a crude $C_6$-$C_{16}$ aliphatic diol comprising distilling one or more times a crude $C_6$-$C_{16}$ aliphatic diol that comprises a monocyclic aliphatic diol represented by the following formula:

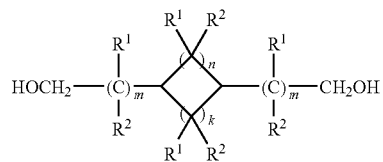

wherein each $R^1$ is independently selected from hydrogen, hydroxy, and $C_1$-$C_6$ monovalent hydrocarbyl radicals; each $R^2$ is independently selected from hydrogen, hydroxy, and $C_1$-$C_6$ hydrocarbyl radicals; n is an integer from 0 to 6; k is an integer from 0 to 6; n+k is greater than 2; and each m is independently an integer from 0 to 3, and further comprising, in addition to the diol, one or more impurities selected from phenols and aliphatic mono-ols, esters, carboxylic acids, and hemiacetals, and mixtures thereof, in the presence of an alkali metal compound and/or an alkaline earth metal compound under distillation conditions sufficient to obtain a purified $C_6$-$C_{16}$ aliphatic diol.

2. The process of claim 1 wherein the crude $C_6$-$C_{16}$ aliphatic diol comprises from about 60 to about 80 weight percent $C_6$-$C_{16}$ aliphatic diol and one or more of the following impurities in the following percentages by weight:

| | |
|---|---|
| Mono-ols | 0.5 to 10 percent |
| Esters | 1 to 5 percent |
| Carboxylic acids | 0.5 to 10 percent |
| Hemiacetals/Lactones | 1 to 5 percent |
| Phenols | less than 1 percent |
| Lights | 15 to 25 percent |
| Intermediates* | 0.1 to 5 percent |
| (*other than mono-ols, hemiacetals and lactones) | |
| Heavies | 0.1 to 5 percent. |

3. The process of claim 1 wherein the crude $C_6$-$C_{16}$ aliphatic diol comprises cis/trans-(1,3)(1,4)-cyclohexanedimethanol.

4. The process of claim 1 wherein the alkali metal compound comprises an alkali metal hydroxide and wherein the alkaline earth metal compound comprises an alkaline earth metal hydroxide.

5. The process of claim 1 wherein the alkali metal compound is selected from the group consisting of sodium hydroxide, potassium hydroxide, cesium hydroxide, lithium hydroxide, sodium hydrogen carbonate, sodium carbonate, potassium carbonate, cesium carbonate, lithium carbonate, sodium acetate, potassium acetate, cesium acetate, lithium acetate, sodium stearate, potassium stearate, cesium stearate, lithium stearate, sodium borohydride, sodium phenylborate, sodium benzoate, potassium benzoate, cesium benzoate, lithium benzoate, disodium hydrogen phosphate, dipotassium hydrogen phosphate, dilithium hydrogen phosphate, disodium phenylphosphate, disodium salt of bisphenol A, dipotassium salt of bisphenol A, dicesium salt of bisphenol A, dilithium salt of bisphenol A, sodium phenolate, potassium phenolate, cesium phenolate, lithium phenolate, and mixtures thereof.

6. The process of claim 1 wherein the alkaline earth metal compound is selected from the group consisting of magnesium hydroxide, calcium hydroxide, strontium hydroxide, barium hydroxide, magnesium hydrogen carbonate, calcium hydrogen carbonate, strontium hydrogen carbonate, barium hydrogen carbonate, magnesium acetate, calcium acetate, strontium acetate, barium acetate, magnesium stearate, calcium stearate, calcium benzoate, and magnesium phenylphosphate, and mixtures thereof.

7. The process of claim 1 wherein the quantity of alkali metal compound and/or alkaline earth metal compound is greater than 1.0 equivalent and less than 2.5 equivalents per equivalent of acid in the diol.

8. The process of claim 1 wherein the quantity of alkali metal compound and/or alkaline earth metal compound is greater than 100 parts per million (ppm) and less than 5,000 ppm, based on the weight of the diol.

9. The process of claim 1 wherein a first distillation is conducted in a distillation column to remove lights at a temperature from 80° C. to 210° C. at the bottom of the column and from 20° C. to 120° C. at the top of the column, and about 1 atmosphere (101 kPa) pressure.

10. The process of claim 1 wherein after removal of lights a second distillation is conducted in a distillation column at a bottom temperature ranging from 165° C. to 250° C., and a head temperature ranging from 160° C. to 180° C. at a subatmospheric pressure ranging from 15 torr (2.0 kPa) to 50 torr (6.7 kPa).

11. The process of claim 10 wherein the second distillation is conducted in a distillation column comprising from 30 to 100 theoretical trays.

12. The process of claim 10 wherein the second distillation is conducted at a reflux ratio ranging from 1:10 to 10:1.

13. The process of claim 1 wherein the one or more distillations are conducted in a continuous mode of operation.

14. The process of claim 1 wherein the purified diol is recovered at each distillation stage in a yield of greater than 90 percent, based on the weight of the diol fed to the distillation.

15. The process of claim 1 wherein the purified diol exhibits a total acidity of less than 500 parts per million (ppm) (less than 0.05 weight percent), calculated as acetic acid, based on the weight of the diol.

16. The process of claim 1 wherein the purified diol has a color rated less than 10 per test method ASTM D 1209-00.

17. The process of claim 1 wherein the $C_6$-$C_{16}$ aliphatic diol comprises cis/trans-(1,3)(1,4)-cyclohexanedimethanol, and wherein the alkali metal compound comprises potassium hydroxide.

18. The process of claim 17 wherein the alkali metal compound is employed in an amount ranging from greater than 1.25 to less than 2.50 equivalents per equivalent of acid in the diol.

19. The process of claim 17 wherein the process is conducted in a continuous mode of operation.

* * * * *